(12) United States Patent
Vallejos et al.

(10) Patent No.: US 8,399,714 B2
(45) Date of Patent: Mar. 19, 2013

(54) PROCESS FOR THE SYNTHESIS OF POLYHYDROXYSTILBENE COMPOUNDS

(75) Inventors: Jean-Claude Vallejos, La Ciotat (FR); Alain Schouteeten, Ezanville (FR); Didier Wilhelm, Issy les Moulineaux (FR)

(73) Assignee: Clariant Speciality Fine Chemicals (France), Nanterre (FR)

( * ) Notice: Subject to any disclaimer, the term of this patent is extended or adjusted under 35 U.S.C. 154(b) by 236 days.

(21) Appl. No.: 12/680,752

(22) PCT Filed: Sep. 23, 2008

(86) PCT No.: PCT/EP2008/062693
§ 371 (c)(1), (2), (4) Date: Jul. 29, 2010

(87) PCT Pub. No.: WO2009/043761
PCT Pub. Date: Apr. 9, 2009

(65) Prior Publication Data
US 2010/0324342 A1    Dec. 23, 2010

(30) Foreign Application Priority Data
Oct. 3, 2007    (FR) .................... 07 58026

(51) Int. Cl.
C07C 37/055    (2006.01)
(52) U.S. Cl. ........................ 568/729
(58) Field of Classification Search ........ 568/729
See application file for complete search history.

(56) References Cited

U.S. PATENT DOCUMENTS

| | | | |
|---|---|---|---|
| 3,256,336 | A | 6/1966 | Lange |
| 6,407,142 | B1 | 6/2002 | Courbriere et al. |
| 6,844,471 | B2 | 1/2005 | Deshpande et al. |
| 7,253,324 | B1 * | 8/2007 | Majeed et al. ............ 568/805 |
| 8,101,804 | B2 | 1/2012 | Schouteeten et al. |
| 2004/0015020 | A1 | 1/2004 | Deshpande et al. |

FOREIGN PATENT DOCUMENTS

| | | |
|---|---|---|
| CN | 1663939 | 9/2005 |
| EP | 1 466 884 | 10/2004 |
| EP | 1884508 | 2/2008 |
| WO | WO 00/69430 | 11/2000 |
| WO | WO 01/60774 | 8/2001 |
| WO | WO 03/086414 | 10/2003 |
| WO | WO 2005/023740 | 3/2005 |
| WO | WO 2005/069998 | 8/2005 |

OTHER PUBLICATIONS

Journal of Medicinal Chemistry, 30(11), (1987), pp. 2121-2126.
Tetrahedron, 59(18), (2003), pp. 3315-3322.
Chemistry Letters, 11, (1999), pp. 1193-1194.
Journal of the American Chemical Society, 126(32), (2004), pp. 9882-9883.
Chemistry and Pharmaceutical Bulletin, (1992), 40(10), pp. 2842-2844.
Journal of Organic Chemistry, (2002), 67, pp. 4627-4629.
Roberts, et al., Canadian Journal of Chemistry, (81), (2003), pp. 709-722.
Talvitie, et al., Acta Chemica Scandinavia, (50), (1996), pp. 1143-1146.

(Continued)

*Primary Examiner* — Brian J Davis
(74) *Attorney, Agent, or Firm* — Tod A. Waldrop

(57) ABSTRACT

The invention relates to a process for the synthesis of stilbene derivatives of formula (I)-(E) or (I)-(Z)

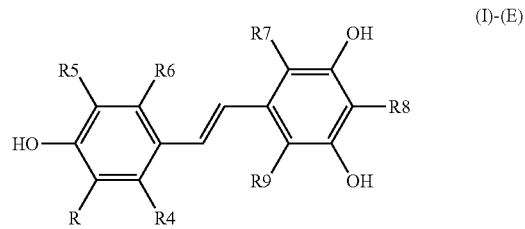

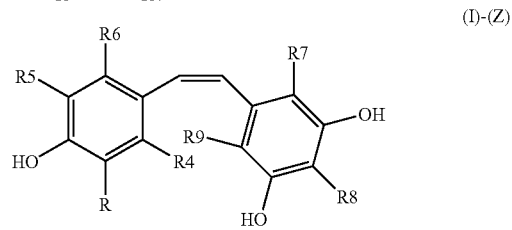

in which R represents hydrogen or an OH group,
by deprotection in the presence of an aluminum halide and of a tertiary amine of a compound of formula (II)-(E) or (II)-(Z)

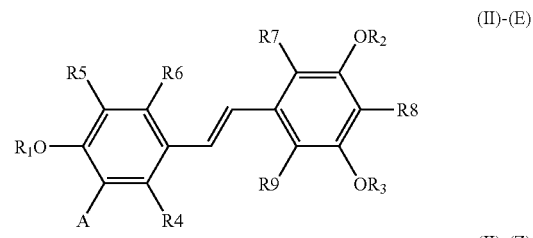

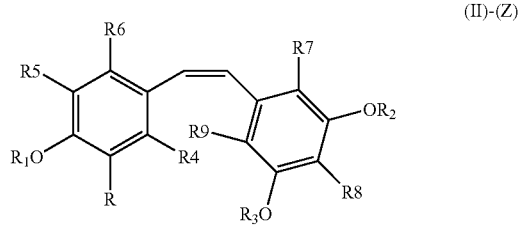

in which A represents hydrogen or an OR'$_1$ group, and R$_1$, R$_2$, R$_3$ and R'$_1$ independently represent an alkyl or aralkyl group.

22 Claims, No Drawings

OTHER PUBLICATIONS

INPI Preliminary Search Report for FR0653178, dated Mar. 30, 2007.
Extended European Search for EP 09 01 5839, dated Aug. 2, 2010.
T. Akiyama, H. Hirofuji, S. Ozaki, AlCl3-N,N-Dimethylaniline: a new benzyl and allyl ether cleavage reagent, Tetrahedron Letters, vol. 32, No. 10, pp. 1321-1324, 1991.
Robert G. Lange, Cleavage of Alkyl o-Hydroxyphenyl Ethers, Journal of Organic Chemistry, 1962, 27(6), 2037-2039.
Roberti Marinella, et al., "Synthesis and biological evaluation of resveratrol and analogues as apoptosis-inducing agents", J. Med. Chem., N°46, 2003, pp. 3546-3554.
J.Chem.Soc. (1944), 330.
Tetrahedron Lett., 44, 1 (2003), 193-98.
J. Org. Chem., 62, 2 (1997), 417-21.
J.Agric.Food Chem., 47, 10 (1999), 3974-77.
INPI Preliminary Search Report for FR0758026, dated May 28, 2008.
English Abstract for CN 1663939, Mar. 2, 2004.
International Search Report for PCT/EP2008/062693, dated Feb. 19, 2009.
English Abstract for EP 1 466 884, publication date Oct. 13, 2004.
Advanced Organic Chemistry, Reactions, Mechanisms and Structure, John Wiley & Sons, 4th edition, 1992, pp. 491-493.
Advanced Organic Chemistry, Reactions, Mechanisms and Structure, John Wiley & Sons, 4th edition, 1992, p. 629.
Advanced Organic Chemistry, Reactions, Mechanisms and Structure, John Wiley & Sons, 4th edition, 1992, pp. 910-918.
Advanced Organic Chemistry, Reactions, Mechanisms and Structure, John Wiley & Sons, 4th edition, 1992, pp. 1019-1021.
International Search Report and Written Opinion of the International Searching Authority for PCT/EP2007/057650, Oct. 24, 2007.
Translation of Russian Federal Service for Intellectual Property Office Action for PCT/EP2007/057650, 2009.

* cited by examiner

PROCESS FOR THE SYNTHESIS OF POLYHYDROXYSTILBENE COMPOUNDS

A subject-matter of the present invention is a novel process of the synthesis of polyhydroxystilbene compounds.

The invention relates more particularly to a process for the synthesis of resveratrol and piceatannol.

Polyhydroxystilbenes are compounds which are found in various plants and which have received particular attention because they exhibit a great variety of therapeutic properties.

These derivatives include resveratrol (E-3,5,4'-trihydroxystilbene) and piceatannol (E-3,5,3',4'-tetrahydroxystilbene) of formulae:

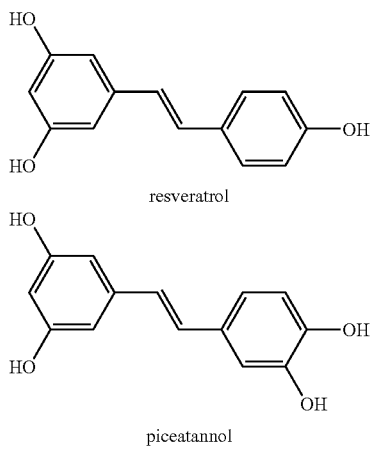

resveratrol piceatannol

Resveratrol and piceatannol are compounds belonging to the class of the polyphenols, which are known to exert antioxidant effects capable of preventing or delaying the detrimental effects of oxidative stress.

In the therapeutic field, resveratrol is listed as platelet antiaggregant, antiinflammatory or vasodilator or as cell proliferation inhibitor.

The majority of the routes used to produce polyhydroxystilbenes require the protection of the phenol functional groups in the form of ether derivatives. Protection is most generally obtained by methyl, methylene, isopropyl or benzyl groups. The synthesis of the polyhydroxystilbenes requires, lastly, a stage of deprotection in order to release the phenol functional groups. The stage of deprotection of the phenol ethers is generally easily carried out in the case of simple derivatives, such as anisole, with aluminium chloride, as in J. Chem. Soc. (1944), 330. However, this reaction is difficult in the case in particular of stilbene derivatives due to the presence of the double bond and more particularly when the molecule has activating groups (that is to say, electron-donating groups) on the aromatic rings of the molecule, such as ether groups. The use of strong acids, such as hydrobromic acid or aluminium chloride, the commonest and cheapest of the Lewis acids, results in significant decomposition of the molecule during these deprotection reactions. In the more specific case of benzyl ethers, deprotection is carried out by hydrogenolysis, which results, in the specific case of stilbene derivatives, in hydrogenation of the double bond.

In order to overcome these disadvantages, in the case of these stilbene derivatives, use is generally made, in O-demethylation or O-debenzylation reactions, of boron tribromide, as in WO2003/086414, or boron trichloride in the presence of tetrabutylammonium iodide, as in Tetrahedron Lett., 44, 1 (2003), 193-98, and, in the specific case of isopropyl groups, boron trichloride alone, as in Tetrahedron, 59 (2003), 3315-21. However, $BCl_3$, like $BBr_3$, are expensive reagents which are dangerous to use industrially.

Other reagents, such as methylmagnesium iodide, as in J. Org. Chem., 62, 2 (1997), 417-21, or pyridinium hydrochloride, as in J. Agric. Food Chem., 47, 10 (1999), 3974-77, use large amounts of reagents and severe reaction conditions (high temperature) for yields which are generally very mediocre.

Some authors use aluminium chloride in pyridine as reagent and solvent in order to obtain resveratrol at temperatures of 165-170° C., as in Patent CN 1663939. However, in addition to very specific reaction conditions, this solvent is toxic and to be avoided for industrial use. It is the same for the reaction of Akiyama et al., specific for O-debenzylation reactions, which uses aluminium chloride and N,N-dimethylaniline as reagents and which is reported, for example in J. Med. Chem. (2003), 46 (16), 3547, for synthesizing in particular resveratrol and piceatannol. However, the aromatic amine is expensive, highly toxic and difficult to remove, rendering this method of little interest industrially.

Considering that none of the solutions described above is truly satisfactory from an industrial viewpoint, the Applicant Company has looked for a method which is more suitable for the deprotection of alkoxy- or aralkoxystilbene derivatives, more particularly for the purpose of the synthesis of resveratrol and piceatannol.

A subject-matter of the present invention is thus a process for the synthesis of an (E)-stilbene derivative of formula (I)-(E) or a (Z)-stilbene derivative of formula (I)-(Z)

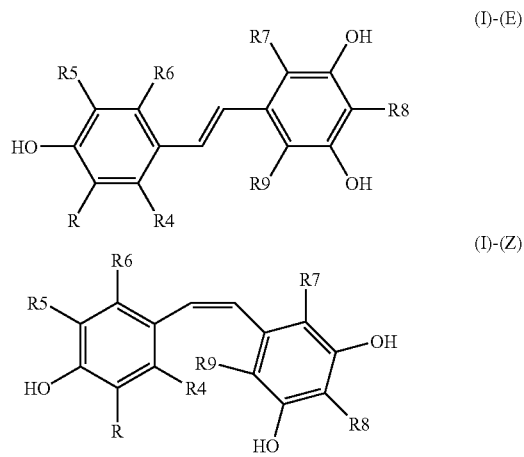

in which:
R represents hydrogen or an OH group,
$R_4$, $R_5$, $R_6$, $R_7$, $R_8$ and $R_9$ independently represent a hydrogen or a substituent chosen from:
a halogen;
a nitro group;
a linear or branched $C_1$-$C_6$ alkyl group;
a linear or branched $C_2$-$C_6$ alkenyl group;
a $C_3$-$C_{10}$ cycloalkyl group;
a cycloalkylalkyl group in which the cycloalkyl and alkyl groups are as defined above;
a monocyclic, bicyclic or tricyclic $C_6$-$C_{14}$ aryl group;
a $C_7$-$C_{16}$ aralkyl group;
a C(=O)$R_{10}$ group in which $R_{10}$ represents a linear or branched $C_1$-$C_6$ alkyl group, a $C_3$-$C_{10}$ cycloalkyl group, a cycloalkylalkyl group in which the cycloalkyl and alkyl groups are as defined above, a monocyclic, bicyclic or tricyclic $C_6$-$C_{14}$ aryl group, a $C_7$-$C_{16}$ aralkyl group, an $OR_{11}$ group in which $R_{11}$ represents a hydrogen, a linear or branched $C_1$-$C_6$ alkyl group, a $C_3$-$C_{10}$ cycloalkyl group, a cycloalkylalkyl group in which the cycloalkyl and alkyl groups are as defined above, a monocyclic, bicyclic or tricyclic $C_6$-$C_{14}$ aryl group or a $C_7$-$C_{16}$ aralkyl group, or an $NR_{12}R_{13}$ group in which $R_{12}$ and $R_{13}$ independently represent a hydrogen, a linear or branched $C_1$-$C_6$ alkyl group, a $C_3$-$C_{10}$ cycloalkyl group, a cycloalkylalkyl group in which the cycloalkyl and alkyl groups are as defined above, a monocyclic, bicyclic or tricyclic $C_6$-$C_{14}$ aryl group or a $C_7$-$C_{16}$ aralkyl group;

all the above alkyl, alkenyl, cycloalkyl, cycloalkylalkyl, aryl or aralkyl radicals being unsubstituted or substituted, by deprotection of a compound of formula (II)-(E) or (II)-(Z)

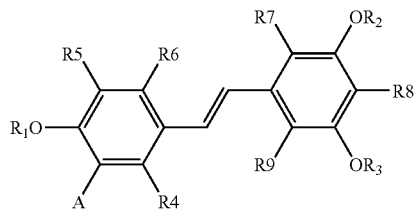

(II)-(E)

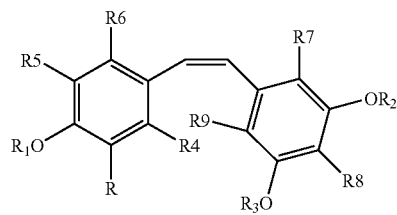

(II)-(Z)

in which A represents hydrogen or an $OR'_1$ group and $R_1$, $R_2$, $R_3$ and $R'_1$ independently represent a linear or branched $C_1$-$C_6$ alkyl group or a $C_7$-$C_{16}$ aralkyl group, optionally substituted on the aryl part by one or more $C_1$-$C_4$ alkoxy or halogen groups, characterized in that the deprotection is carried out by the use of an aluminium halide and of a tertiary amine of formula $NR_aR_bR_c$ in which $R_a$, $R_b$ and $R_c$ independently represent a linear or branched $C_1$-$C_4$ alkyl group.

According to a preferred aspect, the invention also relates to a process for the synthesis of an (E)-stilbene derivative of formula (I)

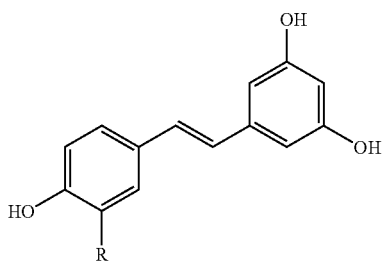

(I)

in which R represents hydrogen or an OH group, by deprotection of a compound of formula (II)

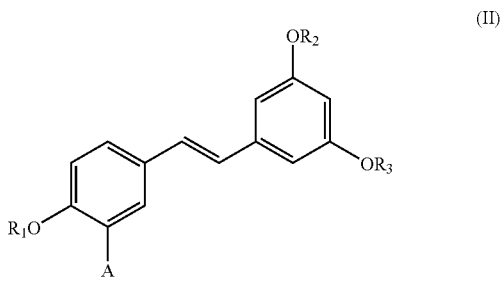

(II)

in which A represents hydrogen or an $OR'_1$ group and $R_1$, $R_2$, $R_3$ and $R'_1$ independently represent a linear or branched $C_1$-$C_6$ alkyl group or a $C_7$-$C_{16}$ aralkyl group, optionally substituted on the aryl part by one or more $C_1$-$C_4$ alkoxy or halogen groups, characterized in that the deprotection is carried out by the use of an aluminium halide and of a tertiary amine of formula $NR_aR_bR_c$ in which $R_a$, $R_b$ and $R_c$ independently represent a linear or branched $C_1$-$C_4$ alkyl group.

In the present description, the term "linear or branched $C_1$-$C_6$ alkyl group" is understood to mean, for example, a methyl, ethyl, propyl, isopropyl, butyl, isobutyl, sec-butyl, tert-butyl, pentyl or hexyl group.

The halogen radical means Cl, Br, F or I.

The term "linear or branched $C_1$-$C_4$ alkyl group" is understood to mean, for example, a methyl, ethyl, propyl, isopropyl, butyl, isobutyl, sec-butyl or tert-butyl group.

The term "linear or branched $C_2$-$C_6$ alkenyl group" is understood to mean, for example, an ethenyl or vinyl, propenyl or allyl, 1-propenyl, n-butenyl, isobutenyl, 3-methylbut-2-enyl, n-pentenyl or hexenyl group.

The term "$C_1$-$C_4$ alkoxy group" denotes, for example, a methoxy, ethoxy, propoxy or butoxy group.

The term "$C_3$-$C_{10}$ cycloalkyl group" is understood to mean, for example, a cyclopropyl, cyclobutyl, cyclopentyl or cyclohexyl group.

The term "cycloalkylalkyl group" is understood to mean, for example, a cyclopropylmethyl, cyclobutylmethyl, cyclopentylmethyl, cyclohexylmethyl, cycloheptylmethyl, cyclopropylethyl or cyclohexylethyl group.

The term "monocyclic, bicyclic or tricyclic $C_6$-$C_{14}$ aryl group" is understood to mean, for example a phenyl, naphthyl, indenyl or anthracenyl group.

The term "$C_7$-$C_{16}$ aralkyl group" is understood to denote, for example, a benzyl, 1-phenylethyl, naphthalenylmethyl or 1-naphthalenylethyl group.

The process of the invention applies particularly to the use of the compounds of formula (II)-(E) or (II)-(Z) in which $R_1$, $R_2$, $R_3$ and $R'_1$ independently represent a linear or branched $C_1$-$C_3$ alkyl group or a benzyl group optionally substituted on the phenyl part by one or more $C_1$-$C_4$ alkoxy groups and very particularly to the use of the compounds of formula (II)-(E) or (II)-(Z) in which $R_1$, $R_2$, $R_3$ and $R'_1$ independently represent a methyl group or benzyl group, $R_4$, $R_5$, $R_6$, $R_7$, $R_8$ and $R_9$ being as defined above.

According to a preferred aspect, the process of the invention applies to the use of the compounds of formula (II) in which $R_1$, $R_2$, $R_3$ and $R'_1$ independently represent a linear or branched $C_1$-$C_3$ alkyl group or a benzyl group optionally substituted on the phenyl part by one or more $C_1$-$C_4$ alkoxy groups and very particularly to the use of the compounds of formula (II) in which $R_1$, $R_2$, $R_3$ and $R'_1$ independently represent a methyl group or a benzyl group.

In the present invention, use is made of an aluminium halide which can be chosen from aluminium chloride, aluminium bromide and aluminium iodide, aluminium chloride being preferred.

According to a preferred aspect of the invention, use is made of a tertiary amine which can be chosen from triethylamine, tripropylamine, tributylamine, N,N-dimethylethylamine, N,N-diethylmethylamine and N,N-dimethylbutylamine, triethylamine being preferred.

The molar ratio of the aluminium halide:tertiary amine reagents used in the process according to the invention can vary between 1:1 and 1:4, preferably between 1:1 and 1:2 and very particularly between 1:1.5 and 1:1.6.

Generally, use is made of between 1 and 10 molar equivalents of aluminium halide and between 1 and 20 molar equivalents of tertiary amine per ether group to be deprotected in the compounds of formula (II)-(E), (II)-(Z) or (II), preferably between 1 and 4 molar equivalents of aluminium halide and between 1 and 6 molar equivalents of tertiary amine per ether group to be deprotected and very particularly between 2 and 2.2 molar equivalents of aluminium halide and between 3 and 3.5 molar equivalents of tertiary amine per ether group to be deprotected.

In accordance with the invention, the process according to the invention can be employed without solvent or with the use of solvents not comprising hydroxyl groups and not comprising oxygen atoms. Preferably, a solvent or a mixture of solvents is used. Mention may more particularly be made, as examples of solvents suitable for the present invention, of halogenated aliphatic hydrocarbons or halogenated or nonhalogenated aromatic hydrocarbons. Mention may more particularly be made, as examples of halogenated aliphatic hydrocarbons, of dichloromethane or 1,2-dichloroethane.

Mention may more particularly be made, as examples of halogenated or nonhalogenated aromatic hydrocarbons, of toluene or chlorobenzene.

The preferred solvents are toluene and chlorobenzene and in particular chlorobenzene.

According to a first alternative form of the invention, there are no restrictions on the use of the aluminium halide and tertiary amine. The aluminium halide and the tertiary amine can be introduced in any order.

According to a preferred embodiment of the invention, the aluminium halide is added to the tertiary amine and then the compound of formula (II)-(E), (II)-(Z) or (II) is introduced.

According to another preferred embodiment of the invention, the compound of formula (II)-(E), (II)-(Z) or (II) is added to the tertiary amine and then the aluminium halide is introduced.

According to a second alternative form of the invention, an aluminium halide/tertiary amine complex is formed beforehand and is optionally isolated, before the introduction of the compound of formula (II)-(E), (II)-(Z) or (II). Preferably, the aluminium halide and the tertiary amine are reacted at a temperature of between 50° C.-60° C. for 1 h to 4 h, optionally in a solvent such as described above.

The temperature at which the process of the invention is carried out is generally between 50° C. and 120° C. Use is preferably made of ranges of temperatures of between 80° C. and 100° C.

The reaction time can vary according to the reaction conditions, in particular the temperature, and the constituents. An analysis of the reaction medium by HPLC makes it possible to confirm the disappearance of the compounds of formula (II)-(E), (II)-(Z) or (II).

The compounds of formula (II)-(E), (II)-(Z) or (II) can be obtained by methods known from the prior art, for example in EP 1 466 884, WO 2003/086414 and US 2004/0015020.

The following examples illustrate the invention without having a limiting nature.

EXAMPLE 1

56.2 g of triethylamine (555.4 mmol) are introduced into 20 ml of chlorobenzene in a three-necked round-bottomed flask. A nitrogen atmosphere is applied, the reaction medium is cooled to 0-5° C. and 45 g of anhydrous aluminium chloride (337.5 mmol) are added in small fractions over 30 min. The medium is maintained at ambient temperature for 30 min with stirring and is then brought to 60° C., where this temperature is maintained for 1 h. 10 g of (E)-3,5,4'-trimethoxystilbene (37 mmol) dissolved in 20 ml of chlorobenzene are subsequently added in 1 h. The mixture is maintained at 60° C. with stirring for 4 h and then at 80° C. for 4 h. It is brought back to ambient temperature, separation by settling is carried out and the upper chlorobenzene phase is recovered. The lower phase is slowly added to 100 g of a 50/50 ice/water mixture. The medium is kept stirred for 1 h and is extracted several times with ethyl acetate.

The combined organic phases are washed with water and concentrated to result in 7.6 g of (E)-resveratrol, i.e. a crude yield of 90%. The crude product is dissolved in ethanol at 60° C. and resveratrol is precipitated by addition of water in order to obtain 6 g of precipitate exhibiting a melting point of 262-264° C.

The proton and $^{13}C$ NMR spectra are in agreement with the structure of (E)-resveratrol.

EXAMPLE 2

4.5 g of anhydrous aluminium chloride (33.7 mmol) are introduced, under a nitrogen atmosphere, at ambient temperature and with stirring, into 10.37 g of tributylamine (56 mmol) in a three-necked round-bottomed flask. The medium is brought to 60° C. and is maintained at this value for 4 h. 1 g of (E)-3,5,4'-trimethoxystilbene (3.7 mmol) is then introduced and the reaction medium is brought to 80° C. for 2 h and to 100° C. for 2 h. It is brought back to ambient temperature and then 10 g of a 50/50 water/ice mixture are added. It is maintained at 0-5° C. with stirring for 3 h and extracted 4 to 5 times with 10 ml of methyl ethyl ketone. The combined organic phases are washed with 10 ml of a saturated aqueous sodium bicarbonate solution and then with 10 ml of water. After concentrating the organic phase, an HPLC quantitative determination (external calibration) gives an (E)-resveratrol yield of 75%.

EXAMPLE 3

4 ml of chlorobenzene and 6 g of triethylamine (59.3 mmol) are introduced into a three-necked round-bottomed flask. A nitrogen atmosphere is applied, the mixture is cooled to 0-5° C. and 4.9 g of anhydrous aluminium chloride (36.7 mmol) are introduced in small fractions at this temperature. The medium is brought to 50° C. and is maintained at this temperature for 1 h, and then 2 g of (E)-3,5,4'-tribenzyloxystilbene (4 mmol) dissolved in 5 ml of chlorobenzene are added in 1 h at this temperature. This temperature is maintained for 4 h and then a temperature of 80° C. is maintained for 4 h. The mixture is brought back to ambient temperature, separation by settling is carried out and the heavy phase is recovered and poured onto 20 ml of a 50/50 ice/water mixture. The medium is kept stirred for 2 h and extracted with ethyl acetate. The organic phase is washed with a saturated aqueous sodium bicarbonate solution and then with water and then concentrated to result in 0.93 g of crude (E)-resveratrol, i.e. a practically quantitative yield with respect to the starting tribenzylresveratrol.

EXAMPLE 4

4.5 ml of chlorobenzene and 15.7 g of triethylamine (155.1 mmol; 21 mol. eq.) are introduced into a three-necked round-bottomed flask. A nitrogen atmosphere is applied, the mixture is cooled to 0-5° C. and 12.8 g of anhydrous aluminium chloride (95 mmol; 13 mol. eq.) are added in 30 min. The medium is brought to 60° C. for 1 h. 2.2 g of tetramethylpiceatannol (7.3 mmol) dissolved in 4.5 ml of chlorobenzene are introduced at this temperature over 1 h and the reaction medium is maintained at this temperature for 4 h and then at 80° C. for 4 h. It is brought back to ambient temperature, separation by settling is carried out and the heavy phase is recovered and hydrolysed by running dropwise onto 40 g of a 50/50 water/ice mixture. The mixture is kept stirred at this temperature for 1 h 30. The medium is extracted with 4 times 25 ml of methyl ethyl ketone and the organic phase is washed with a saturated sodium bicarbonate solution and then with water. 1.62 g of crude (E)-piceatannol are recovered in the form of a brown solid.

The product is purified from a 5/95 mixture of methanol/water in order to result in piceatannol exhibiting a melting point of 233-34° C.

The proton and $^{13}$C NMR spectra are in agreement with the structure of (E)-piceatannol.

EXAMPLE 5

5 g of (E)-3,5,4'-trimethoxystilbene (18.5 mmol) are introduced into 20 g of triethylamine (197.6 mmol) in a 100 ml three-necked round-bottomed flask. The mixture is heated to 50° C. under a nitrogen atmosphere and 16 g of anhydrous aluminium chloride (120 mmol) are added in small fractions over 30 min at this temperature. The reaction medium is then brought to 80° C. for 2 h and then to 100° C. for 2 h. It is cooled to approximately 75° C., 10 ml of anhydrous ethanol are slowly added and then, at this temperature of 75° C., 50 ml of water are added in 30 min. The reaction medium is then cooled to ambient temperature, at which it is maintained for 3 h, and the medium is extracted with 1 times 35 ml and 3 times 30 ml of methyl ethyl ketone. The combined organic phases are washed with 30 ml of water, then with 30 ml of a saturated sodium bicarbonate solution and with 30 ml of water. After concentrating the organic phases, 15 ml of absolute ethanol are added, the mixture is heated to reflux and then 46 g of water are added over approximately 1 h, still at reflux. The mixture is cooled down to ambient temperature and left stirring for 3 h. The precipitate is filtered off and washed on the filter with 9 g of a water/ethanol mixture (80/20 by weight).

After drying at 40° C. under vacuum for 24 h, 3.1 g of (E)-resveratrol are obtained, i.e. a yield of 73.4%.

The HPLC and NMR analyses are in agreement with the structure of (E)-resveratrol.

EXAMPLE 6

5.6 g of triethylamine (55.5 mmol) are introduced into 4 ml of methylene chloride. The medium is cooled to 0-5° C. and 4.5 g of anhydrous aluminium chloride (33.5 mmol) are added in small fractions over 15 min with stirring and under a nitrogen atmosphere. The reaction medium is subsequently brought to 50° C. for 4 h. It is cooled and the solvent and the excess amine are concentrated at ambient temperature in order to obtain approximately 8.5 g of a slightly fuming pinkish solid formed of AlCl$_3$/triethylamine complex. 2 ml of chlorobenzene are added to the solid and the mixture is brought to 60° C. 1 g of 3,5,4'-trimethoxystilbene (3.7 mmol) dissolved in 2 ml of chlorobenzene is added at this temperature over one hour. The mixture is maintained at 60° C. for 4 h and then at 80° C. for 2 h. The reaction medium is brought back to ambient temperature and then hydrolysed by addition of 10 g of a water/ice (50/50) mixture. The temperature is maintained at 0-5° C. for 1 h and the medium is extracted several times with ethyl acetate. After concentrating the organic phases, the precipitate obtained is washed with 6 ml of chlorobenzene and dried under vacuum to result in 0.6 g of crude (E)-resveratrol.

The invention claimed is:
1. A process for the synthesis of an (E)-stilbene derivative of formula (I)-(E) or a (Z)-stilbene derivative of formula (I)-(Z)

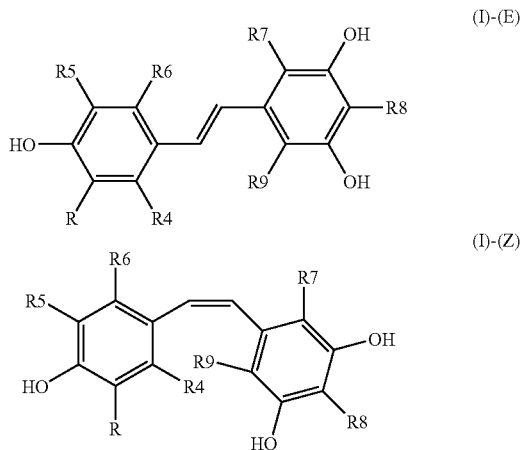

wherein:
R is hydrogen or an OH group,
R$_4$, R$_5$, R$_6$, R$_7$, R$_8$ and R$_9$ are independently a hydrogen or a substituent selected from the group consisting of:
a halogen;
a nitro group;
a linear or branched C$_1$-C$_6$ alkyl group;
a linear or branched C$_2$-C$_6$ alkenyl group;
a C$_3$-C$_{10}$ cycloalkyl group;
a cycloalkylalkyl group wherein the cycloalkyl and alkyl groups are as defined above;
a monocyclic, bicyclic or tricyclic C$_6$-C$_{14}$ aryl group;
a C$_7$-C$_{16}$ aralkyl group; and
a C(=O)R$_{10}$ group wherein R$_{10}$ is a linear or branched C$_1$-C$_6$ alkyl group, a C$_3$-C$_{10}$ cycloalkyl group, a cycloalkylalkyl group wherein the cycloalkyl and alkyl groups are as defined above, a monocyclic, bicyclic or tricyclic C$_6$-C$_{14}$ aryl group, a C$_7$-C$_{16}$ aralkyl group, an OR$_{11}$ group wherein R$_{11}$ is a hydrogen, a linear or branched C$_1$-C$_6$ alkyl group, a C$_3$-C$_{10}$ cycloalkyl group, a cycloalkylalkyl group wherein the cycloalkyl and alkyl groups are as defined above, a monocyclic, bicyclic or tricyclic C$_6$-C$_{14}$ aryl group or a C$_7$-C$_{16}$ aralkyl group, or an NR$_{12}$R$_{13}$ group wherein R$_{12}$ and R$_{13}$ independently are a hydrogen, a linear or branched $C_1$-$C_6$ alkyl group, a $C_3$-$C_{10}$ cycloalkyl group, a cycloalkylalkyl group wherein the cycloalkyl and alkyl groups are as defined above, a monocyclic, bicyclic or tricyclic $C_6$-$C_{14}$ aryl group or a $C_7$-$C_{16}$ aralkyl group;

wherein all the above alkyl, alkenyl, cycloalkyl, cycloalkylalkyl, aryl or aralkyl radicals may be unsubstituted or substituted, comprising the step of deprotecting a compound of formula (II)-(E) or (II)-(Z)

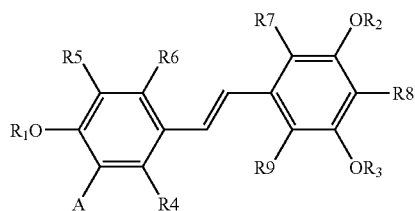

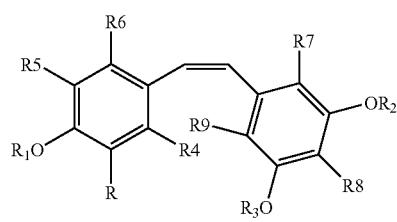

wherein A is a hydrogen or an $OR'_1$ group and $R_1$, $R_2$, $R_3$ and $R'_1$ independently are a linear or branched $C_1$-$C_6$ alkyl group or a $C_7$-$C_{16}$ aralkyl group, optionally substituted on the aryl part by one or more $C_1$-$C_4$ alkoxy or halogen groups, wherein the deprotecting step is carried out by the use of an aluminium halide and of a tertiary amine of formula $NR_aR_bR_c$ wherein $R_a$, $R_b$ and $R_c$ are independently a linear or branched $C_1$-$C_4$ alkyl group.

2. A process according to claim 1 for the preparation of an (E)-stilbene derivative of formula (I)

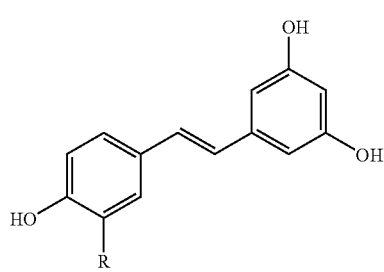

wherein R is a hydrogen or an OH group, comprising the step of deprotecting a compound of formula (II)

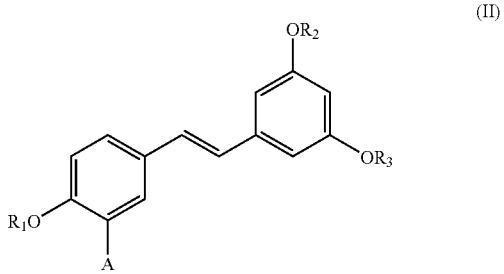

wherein A is a hydrogen or an $OR'_1$, group and $R_1$, $R_2$, $R_3$ and $R'_1$, are independently a linear or branched $C_1$-$C_6$ alkyl group or a $C_7$-$C_{16}$ aralkyl group, optionally substituted on the aryl part by one or more $C_1$-$C_4$ alkoxy or halogen groups, wherein the deprotecting step is carried out by the use of an aluminium halide and of a tertiary amine of formula $NR_aR_bR_c$ wherein $R_a$, $R_b$ and $R_c$ are independently a linear or branched $C_1$-$C_4$ alkyl group.

3. A process according to claim 1, wherein $R_1$, $R_2$, $R_3$ and $R'_1$, in the formula (II)-(E) or (II)-(Z) are independently a linear or branched $C_1$-$C_3$ alkyl group or a benzyl group optionally substituted on the phenyl part by one or more $C_1$-$C_4$ alkoxy or halogen groups, and wherein $R_4$, $R_5$, $R_6$, $R_7$, $R_8$ and $R_9$ are as defined above.

4. A process according to claim 2, wherein $R_3$ and $R'_1$ in the formula (II) are independently a linear or branched $C_1$-$C_3$ alkyl group or a benzyl group optionally substituted on the phenyl part by one or more $C_1$-$C_4$ alkoxy or halogen groups.

5. A process according to claim 2, wherein $R_1$, $R_2$, $R_3$ and $R'_1$ in the formula (II)-(E) or (II)-(Z) or (II) are independently a methyl group or a benzyl group.

6. A process according to claim 1, wherein the aluminium halide is selected from the group consisting of aluminium chloride, aluminium bromide and aluminium iodide.

7. A process according to claim 6, wherein the aluminium halide is aluminium chloride.

8. A process according to claim 1, wherein the tertiary amine is selected from the group consisting of triethylamine, tripropylamine, tributylamine, N,N-dimethylethylamine, N,N-diethylmethylamine and N,N-dimethylbutylamine.

9. A process according to claim 8, wherein the tertiary amine is triethylamine.

10. A process according to claim 1, wherein the aluminium halide to tertiary amine molar ratio is between 1:1 and 1:2.

11. A process according to claim 10, wherein the aluminium halide to tertiary amine molar ratio is between 1:1.5 and 1:1.6.

12. A process according to claim 1, wherein between 1 and 10 molar equivalents of aluminium halide and between 1 and 20 molar equivalents of tertiary amine per ether group to be deprotected in the compounds of formula (II)-(E) or (II)-(Z) is used.

13. A process according to claim 12, wherein between 1 and 4 molar equivalents of aluminium halide and between 1 and 6 molar equivalents of tertiary amine per ether group to be deprotected in the compounds of formula (II)-(E) or (II)-(Z) is used.

14. A process according to claim 1, wherein an aluminium halide/tertiary amine of formula $NR_aR_bR_c$ complex is used in the deprotecting step.

15. A process according to claim 1, wherein the deprotecting step is carried out in the presence of at least one solvent.

16. A process according to claim 15, wherein the solvent is chlorobenzene or toluene.

17. A process according to claim 1, wherein the deprotecting step is carried out at a temperature of between 50° C. and 120° C.

18. A process according to claim 4, wherein $R_1$, $R_2$, $R_3$ and $R'_1$ in the formula (II)-(E) or (II)-(Z) or (II) are independently a methyl group or a benzyl group.

19. A process according to claim 2, wherein between 1 and 10 molar equivalents of aluminium halide and between 1 and 20 molar equivalents of tertiary amine per ether group to be deprotected in the compound of formula (II) is used.

20. A process according to claim 19, wherein between 1 and 4 molar equivalents of aluminium halide and between 1 and 6 molar equivalents of tertiary amine per ether group to be deprotected in the compound of formula (II) is used.

21. A process according to claim 1, wherein the deprotecting step is carried out at a temperature of between 80° C. and 100° C.

22. A process according to claim 1, wherein the deprotecting step is carried out without solvent.

* * * * *